United States Patent
Pissarnitski et al.

(10) Patent No.: US 9,464,103 B2
(45) Date of Patent: Oct. 11, 2016

(54) SPIROCYCLIC SULFONES AS GAMMA SECRETASE INHIBITORS

(71) Applicant: MERCK SHARP & DOHME CORP., Rahway, NJ (US)

(72) Inventors: Dmitri Pissarnitski, Scotch Plains, NJ (US); Zhiqiang Zhao, Scotch Plains, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/647,769

(22) PCT Filed: Nov. 22, 2013

(86) PCT No.: PCT/US2013/071370
§ 371 (c)(1),
(2) Date: May 27, 2015

(87) PCT Pub. No.: WO2014/085211
PCT Pub. Date: Jun. 5, 2014

(65) Prior Publication Data
US 2015/0307533 A1    Oct. 29, 2015

Related U.S. Application Data

(60) Provisional application No. 61/731,025, filed on Nov. 29, 2012.

(51) Int. Cl.
| | |
|---|---|
| C07D 311/80 | (2006.01) |
| C07F 9/6561 | (2006.01) |
| A61K 31/665 | (2006.01) |
| A61K 45/06 | (2006.01) |
| A61K 31/27 | (2006.01) |
| A61K 31/353 | (2006.01) |
| A61K 31/355 | (2006.01) |
| A61K 31/357 | (2006.01) |
| A61K 31/382 | (2006.01) |
| A61K 31/473 | (2006.01) |
| C07D 491/107 | (2006.01) |
| C07D 493/10 | (2006.01) |
| C07D 495/10 | (2006.01) |
| A61K 31/337 | (2006.01) |
| A61K 31/403 | (2006.01) |

(52) U.S. Cl.
CPC ............. *C07F 9/6561* (2013.01); *A61K 31/27* (2013.01); *A61K 31/337* (2013.01); *A61K 31/353* (2013.01); *A61K 31/355* (2013.01); *A61K 31/357* (2013.01); *A61K 31/382* (2013.01); *A61K 31/403* (2013.01); *A61K 31/473* (2013.01); *A61K 31/665* (2013.01); *A61K 45/06* (2013.01); *C07D 311/80* (2013.01); *C07D 491/107* (2013.01); *C07D 493/10* (2013.01); *C07D 495/10* (2013.01)

(58) Field of Classification Search
None
See application file for complete search history.

(56) References Cited

U.S. PATENT DOCUMENTS

| | | | |
|---|---|---|---|
| 2007/0197581 A1* | 8/2007 | Asberom et al. | C07C 317/14 514/291 |
| 2011/0236400 A1 | 9/2011 | Wu et al. | |
| 2012/0107328 A1 | 5/2012 | Greenlee et al. | |

OTHER PUBLICATIONS

Henley, David. Expert Opin. Pharmacother. (2009) 10:10 1657-1664.*
Martone, Robert. JPET 331 (2009) 598-608.*
Skovronsky, Daniel. Annu. Rev. Pathol. Mech. Dis. (2006) 1:151-170.*

* cited by examiner

*Primary Examiner* — Golam M M Shameem
*Assistant Examiner* — Laura Daniel
(74) *Attorney, Agent, or Firm* — J. Eric Thies; John C. Todaro

(57) ABSTRACT

Disclosed herein are compounds of Formula (I), wherein each of the substituents is given the definition as set forth in the specification and claims. Also disclosed are pharmaceutical compositions containing the compound of Formula (I) and use of the compound in the treatment of neurodegenerative diseases or conditions such as Alzheimer's disease.

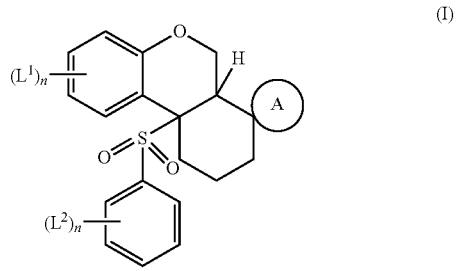

16 Claims, No Drawings

SPIROCYCLIC SULFONES AS GAMMA SECRETASE INHIBITORS

CROSS REFERENCE TO RELATED APPLICATIONS

This application is a U.S. National Phase application under 35 U.S.C. §371 of PCT Application No. PCT/US2013/071370, filed Nov. 22, 2013, which claims priority under 35 U.S.C. §119(e) from U.S. Ser. No. 61/731,025, filed Nov. 29, 2012.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22), suggesting a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer's disease and Down's syndrome*, Proceeding National Academy of Science USA, June 1985, 82(12), p. 4245-4249).

Furthermore, it is known that mutations of APP and presenelin genes, which are observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of Aβ40 and Aβ42 are expected to be agents for controlling progress of Alzheimer's disease or for preventing the disease.

These Aβs are produced when APP is cleaved by beta-secretase and subsequently cleaved by gamma-secretase. In consideration of this, creation of inhibitors of gamma-secretase and beta-secretase has been attempted for the purpose of reducing production of Aβs. Many of these known secretase inhibitors are peptides or peptidomimetics such as L-685,458. L-685,458, an aspartyl protease transition state mimic, is a potent inhibitor of γ-secretase activity (Biochemistry, Aug. 1, 2000, 39(30), p. 8698-8704).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

Compounds of this invention herein termed gamma-secretase inhibitors have the structure of Formula (I);

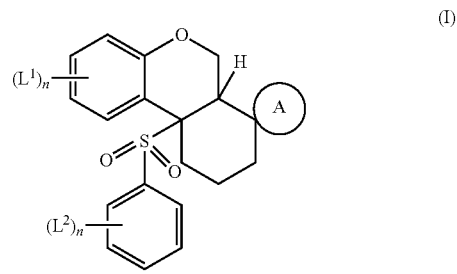

(I)

wherein:
A is a 4 to 7 membered spirocyclic ring comprising at least one heteroatom selected from the group consisting of N, O, S, S(O)$_2$, P(O)R$^1$, and N—S(O)$_2$—R$^1$, wherein the spirocyclic ring is optionally substituted with 1 to 3 substituents selected from the group consisting of C1-3alkyl and =O;
R$^1$ is C1-6alkyl optionally substituted with halo;
Each L$^1$ is independently selected from the group consisting of 1) C1-3alkyl optionally substituted with halo, and 2) halo;
Each L$^2$ is independently selected from the group consisting of 1) C1-3alkyl optionally substituted with halo, and 2) halo; and
n is 0 to 3.

In an embodiment, the present invention provides for pharmaceutical compositions comprising at least one compound of Formula (I). In another embodiment, the present invention provides for methods for inhibiting gamma-secretase activity comprising administering a therapeutically effective amount of at least one compound of Formula (I) to a patient afflicted with a disease or condition amenable to treatment by inhibition of gamma-secretase, e.g., Alzheimer's disease.

DETAILED DESCRIPTION OF THE INVENTION

As used above, and throughout this disclosure, the following terms, unless otherwise indicated, shall be understood to have the following meanings:

"At least one" means there is at least one, and examples include 1, 2 or 3.

"One or more" means the same as "at least one."

"Patient" and "subject" means an animal, such as a mammal, e.g., a human being, and is preferably a human being.

"Alkyl" means an aliphatic hydrocarbon group, which may be straight or branched and comprising about 1 to about 6 carbon atoms in the chain or about 1 to about 2 or 3 carbon atoms in the chain. Branched means that one or more lower alkyl groups such as methyl, ethyl or propyl, are attached to a linear alkyl chain. Non-limiting examples of suitable alkyl groups include methyl, ethyl, n-propyl, isopropyl and t-butyl.

"Halo" means fluorine, chlorine, bromine, or iodine. Fluorine, chlorine and bromine are preferred. A substituent which is a halogen atom means —F, —Cl, —Br, or —I, and "halo" means fluoro, chloro, bromo or iodo substituents bonded to the moiety defined, e.g., "haloalkyl" means an alkyl, as defined above, wherein one or more of the bonding positions on the alkyl moiety typically occupied by hydrogen atoms are instead occupied by a halo group, e.g., trifluoromethyl.

"Spirocyclic" ring means a ring connected to another ring through just one atom.

The term "optionally substituted" means optional substitution with the specified groups, radicals or moieties. For example, a phenyl optionally substituted with an indicated group of substituents includes unsubstituted phenyl as well as phenyl substituted with any of the indicated substituents.

It should also be noted that any carbon atom as well as any heteroatom with unsatisfied valences in the text, schemes, examples, Tables, etc. herein is assumed to have the sufficient number of hydrogen atom(s) to satisfy the valences.

"Effective amount" or "therapeutically effective amount" is meant to describe an amount of compound or a composition of the present invention effective in inhibiting the production and/or deposition of amyloid protein, and thus producing the desired therapeutic, ameliorative, inhibitory or preventative effect.

This invention provides compounds that are inhibitors (e.g., antagonists) of gamma-secretase (also termed "γ-secretase") and have the Formula (I):

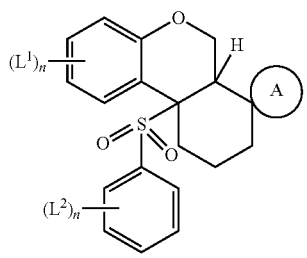

(I)

wherein:
A is a 4 to 7 membered spirocyclic ring comprising at least one heteroatom selected from the group consisting of N, O, S, S(O)$_2$, P(O)R$^1$, and N—S(O)$_2$—R$^1$, wherein the spirocyclic ring is optionally substituted with 1 to 3 substituents selected from the group consisting of C1-3alkyl and =O;
R$^1$ is C1-6alkyl optionally substituted with halo (i.e., a haloalkyl, e.g., —CF$_3$);
Each L$^1$ is independently selected from the group consisting of 1) C1-3alkyl optionally substituted with halo, and 2) halo;
Each L$^2$ is independently selected from the group consisting of 1) C1-3alkyl optionally substituted with halo, and 2) halo; and
n is 0 to 3.

The compounds of the invention have been found to be inhibitors of gamma-secretase activity and are believed to be useful in providing treatment of conditions or diseases which can be treated by inhibition of gamma-secretase activity, for example, Alzheimer's disease, Down's Syndrome, mild cognitive impairment, glaucoma, cerebral amyloid angiopathy, stroke, dementia, microgliosis, brain inflammation, traumatic brain injury and olfactory function loss.

In one embodiment of the compounds of Formula (I), R$^1$ is C1-3alkyl, e.g., methyl.

In another embodiment of the compounds of Formula (I), L$^1$ and L$^2$ are halo.

In another embodiment of the compounds of Formulas (I), L$^1$ is fluoro and L$^2$ is chloro.

In another embodiment, the compounds of Formula (I) have the following Formula (Ia)

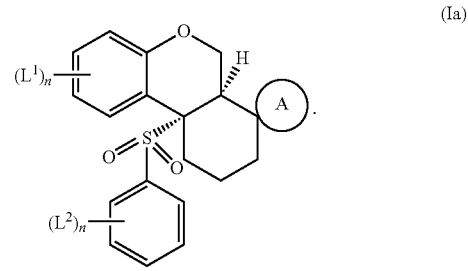

(Ia)

In another embodiment, the compounds of Formulas (I) have the following Formula (II)

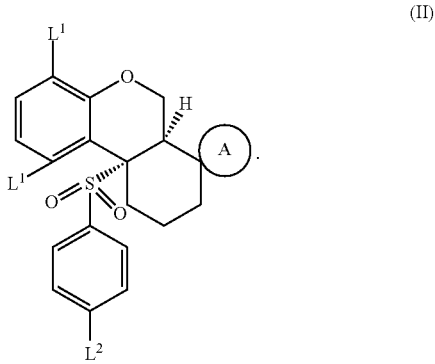

(II)

In another embodiment of the compounds of Formulas (I), (Ia) and (II), A is a 4 to 7 membered spirocyclic ring comprising at least one O heteroatom.

In another embodiment of the compounds of Formulas (I), (Ia) and (II), A is a 5 to 7 membered spirocyclic ring comprising two O heteroatoms.

In another embodiment of the compounds of Formulas (I), (Ia) and (II), A is a 4 to 7 membered spirocyclic ring comprising one N heteroatom.

In another embodiment of the compounds of Formulas (I), (Ia) and (II), A is a 4-7 membered spirocyclic ring comprising one S heteroatom.

In another embodiment of the compounds of Formulas (I), (Ia) and (II), A is a 4-7 membered spirocyclic ring comprising one S(O)$_2$ heteroatom.

In another embodiment of the compounds of Formulas (I), (Ia) and (II), A is a 6-7 membered spirocyclic ring comprising two O heteroatoms and the heteroatom P(O)R$^1$.

In another embodiment of the compounds of Formulas (I), (Ia) and (II), wherein A is a 6-7 membered spirocyclic ring comprising two O heteroatoms and the heteroatom P(O), $R^1$ is methyl.

In another embodiment of the compounds of Formulas (I), (Ia) and (II), $L^1$ and $L^2$ are halo.

In another embodiment of the compounds of Formulas (I), (Ia) and (II), $L^1$ is fluoro and $L^2$ is chloro.

In another embodiment, the compounds of Formulas (I), (Ia) and (II) are selected from the group consisting of -continued

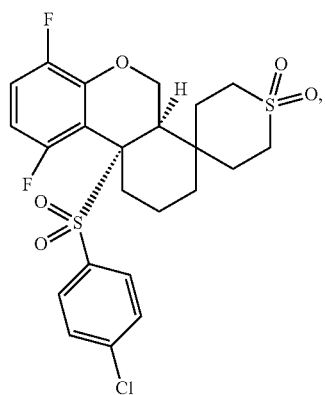

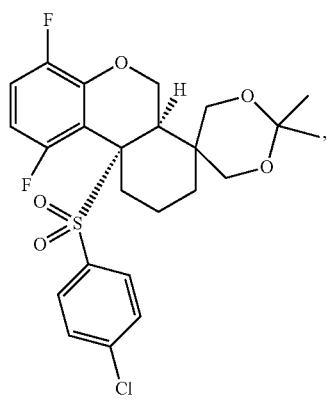

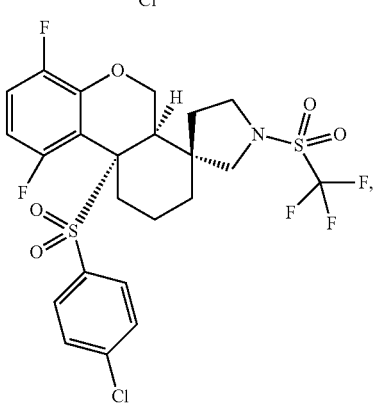

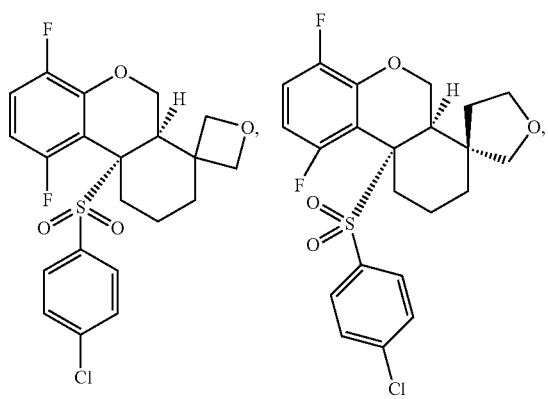

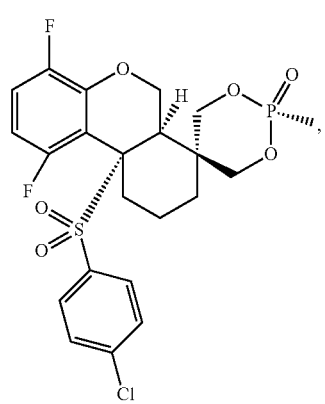

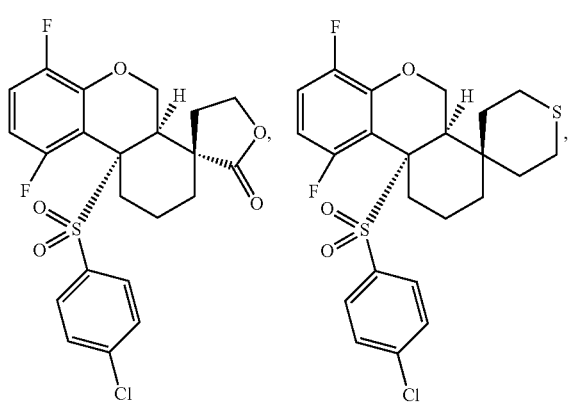

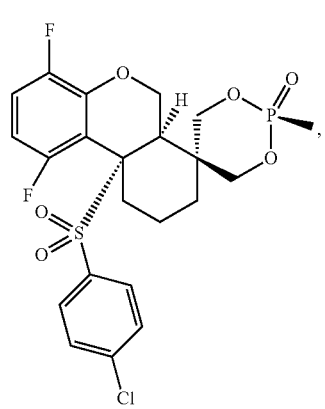

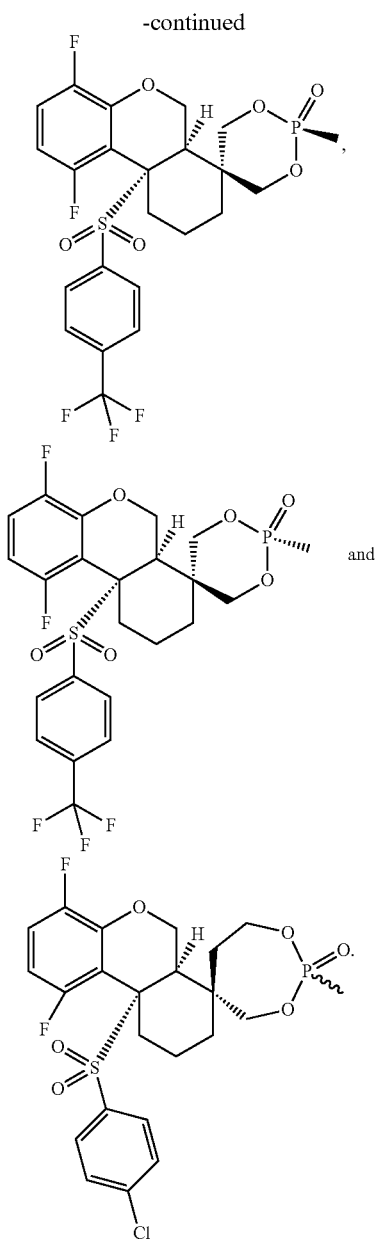

Prodrugs and solvates of the compounds of the invention are also contemplated herein. The term "prodrug", as employed herein, denotes a compound that is a drug precursor that, upon administration to a subject, undergoes chemical conversion by metabolic or chemical processes to yield a compound of Formula (I) or a solvate thereof. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "hydrate" is a solvate wherein the solvent molecule(s) is/are $H_2O$.

All stereoisomers (for example, geometric isomers, optical isomers and the like) of the present compounds (including those of, solvates and prodrugs of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "solvate" "prodrug" and the like, is intended to equally apply to the, solvate and prodrug of enantiomers, stereoisomers, rotamers, tautomers, positional isomers, racemates or prodrugs of the inventive compounds.

Polymorphic forms of the compounds of Formulas (I), (Ia), and (II) and of the solvates and prodrugs of the compounds of Formula (I) are intended to be included in the present invention.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled compounds of Formulas (I), (Ia), and (II) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detection. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically-labeled compounds of Formulas (I), (Ia) and (II) can generally be prepared by following procedures analogous to those disclosed in the Schemes and/or in the Examples herein below, by substituting an appropriate isotopically labeled reagent for a non-isotopically labeled reagent.

Representative compounds of the invention include but are not limited to the compounds and Examples described herein.

The compounds according to the invention have pharmacological properties; in particular, the compounds of Formulas (I), (Ia) and (II) can inhibit gamma-secretase, and therefore may be useful in the treatment or prevention of neurodegenerative diseases, e.g., Alzheimer's disease and other neurodegenerative diseases or conditions as described below.

Pharmaceutical compositions can comprise at least one compound of Formulas (I), (Ia) or (II), and at least one pharmaceutically acceptable carrier. For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active compound. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., herein incorporated by reference in its entirety.

Liquid form preparations include solutions, suspensions and emulsions. Water or water-propylene glycol solutions for parenteral injection or addition of sweeteners and opacifiers for oral solutions, suspensions and emulsions are examples. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably, the pharmaceutical preparation is in a unit dosage form. In such form, the preparation is subdivided into suitably sized unit doses containing appropriate quantities of the active compound, e.g., an effective amount to achieve the desired purpose.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents." The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The quantity of active compound in a unit dose of preparation may be varied or adjusted from about 1 mg to about 1000 mg, preferably from about 1 mg to about 750 mg, more preferably from about 1 mg to about 500 mg, and most preferably from about 1 mg to about 250 mg, according to the particular application. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention will be regulated according to the judgment of the attending clinician considering such factors as age, condition and size of the patient as well as severity of the symptoms being treated. A typical recommended daily dosage regimen for oral administration can range from about 1 mg/day to about 1000 mg/day, in one to four divided doses.

As indicated above, the compounds of the invention may be useful in the treatment of Alzheimer's disease. Accordingly, in another embodiment of this invention a method of treating Alzheimer's disease is provided comprising administering to a patient in need thereof a therapeutically effective amount of at least one compound of Formulas (I), (Ia) or (II).

In another embodiment of the method of treating Alzheimer's disease, the method comprises administering to a patient in need thereof a therapeutically effective amount of at least one compound of Formulas (I), (Ia) or (II) and a therapeutically effective amount of at least one drug selected from the group consisting of BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitor; anti-Abeta vaccine; APP ligands; agents that upregulate insulin cholesterol lowering agents; cholesterol absorption inhibitors; fibrates; LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux.

In another embodiment, a method of treating Alzheimer's disease is provided comprising administering a therapeutically effective amount of at least one compound of Formulas (I), (Ia) or (II) in combination with a therapeutically effective amount of at least one cholinesterase inhibitor (such as, for example, (±)-2,3-dihydro-5,6-dimethoxy-2-[[1-(phenylmethyl)-4-piperidinyl]methyl]-1H-inden-1-one hydrochloride, i.e, donepezil hydrochloride, available as the Aricept® brand of donepezil hydrochloride), to a patient in need of treatment.

The invention also provides for a method of inhibiting the deposition of amyloid beta protein in, on or around neurological tissue, the method comprising administering to a patient in need thereof a therapeutically effective amount of at least one compound of the Formulas (I), (Ia) or (II).

As the compounds of Formulas (I), (Ia) and (II) inhibit gamma-secretase activity, the invention also provides for a method of inhibiting gamma-secretase comprising administering to a patient in need thereof a therapeutically effective amount of at least one compound of the Formulas (I), (Ia) or (II).

As the compounds of Formulas (I), (Ia) and (II) in inhibiting gamma-secretase activity, inhibit amyloid beta production (Aβ40 and Aβ42 production) the invention also provides for a method of inhibiting amyloid beta production comprising administering to a patient in need thereof a therapeutically effective amount of at least one compound of the Formulas (I), (Ia) or (II).

The compounds of Formulas (I), (Ia) and (II) may also be useful in treating a neurodegenerative disease or condition selected from the group consisting of Down's Syndrome, mild cognitive impairment, glaucoma, cerebral amyloid angiopathy, stroke, dementia, microgliosis, brain inflammation, traumatic brain injury and olfactory function loss. The method of treatment comprises administering to a patient in need thereof a therapeutically effective amount of at least one compound of the Formulas (I), (Ia) or (II).

The compounds of Formulas (I), (Ia) and (II) may also be useful in treating cancers such as T-cell acute lymphoblastic leukemia, ovarian cancer, and lung cancers, e.g., non-small-cell lung carcinomas. The method of treatment of one of the aforementioned cancers comprises administering to a patient in need thereof a therapeutically effective amount of at least one compound of the Formulas (I), (Ia) or (II).

The compounds of Formulas (I), (Ia) or (II) may also be useful in treating the aforementioned cancers in combination with a therapeutically effective amount of another pharmaceutically active agent, e.g., a glucocorticoid such as dexamethasone.

EXAMPLES

The invention disclosed herein is exemplified by the following preparations and examples, which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The retention time and observed parent ion are given.

The following solvents, reagents, and conditions may be referred to by their abbreviations in parenthesis:

4-Dimethylaminopyridine (DMAP)
9-Borabicyclo[3.3.1]nonane (9-BBN)
Dichloromethane (DCM)
Diisobutylaluminum hydride (DIBAL-H)
Dimethyl formamide (DMF)
Ethanol (EtOH)
Ethyl acetate (EtOAc)
Isopropyl alcohol (IPA)
Liquid chromatography/mass spectrometry (LCMS)
Mesyl (Ms), i.e., —S(O)$_2$CH$_3$ Methanesulfonyl chloride MsCl
Methanol (MeOH)
Methyl (Me)
Nuclear magnetic resonance spectroscopy (NMR)
Potassium tert-butoxide (t-BuOK)
Preparative thin-layer chromatography (PTLC)
p-Toluenesulfonyl chloride (TsCl)
Pyridinium p-toluenesulfonate (PPTS).
Room temperature (RT)
Tert-butyldimethylsilyl trifluoromethanesulfonate (TBDMSOTf)
Tetrabutyl ammonium fluoride (TBAF)
Tetrahydrofuran (THF)
Triethylamine (Et$_3$N)

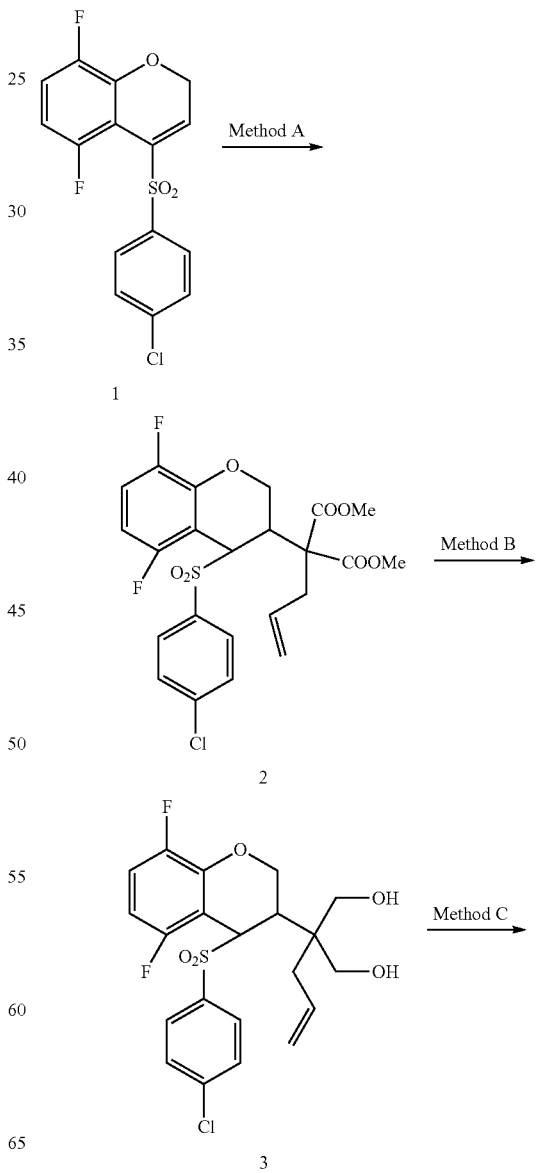

SCHEME 1

13

-continued

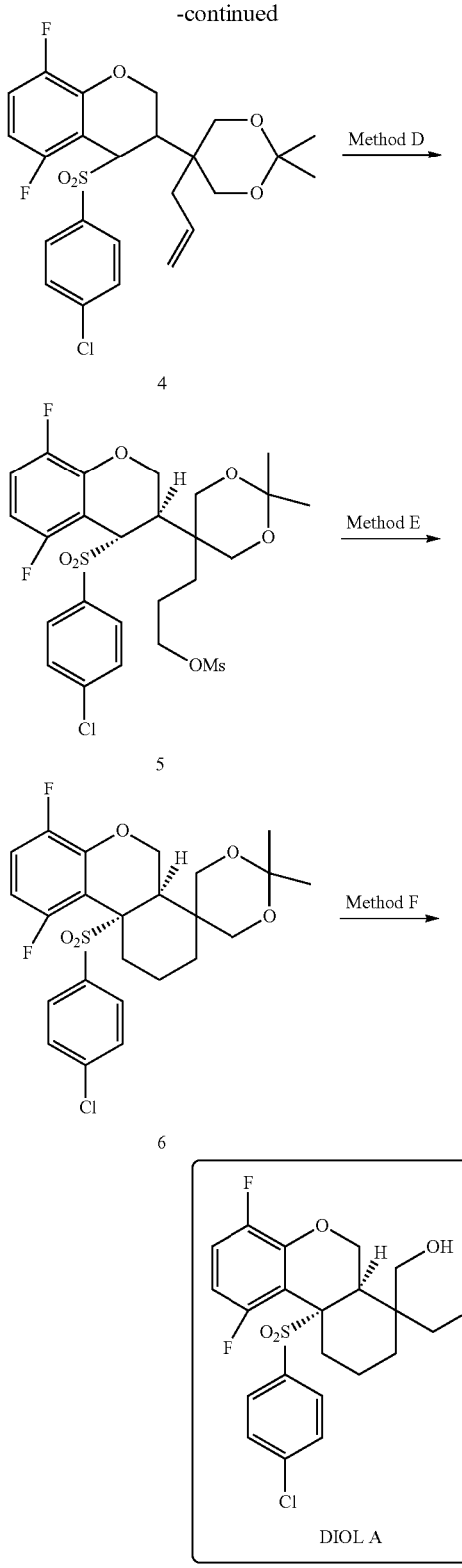

Scheme 1

Method A

To a solution of dimethyl allylmalonate (17.1 g, 99 mmol) in THF (200 mL), was added 12.4 g (90 mmol) of $K_2CO_3$.

14

The resulting suspension was stirred for 10 minutes and compound 1 (prepared according to WO 2007084595) was added as a solid. The reaction was stirred for 2 hours, quenched with water, and extracted with EtOAc twice. The organic phase was washed with water and brine, dried over $Na_2SO_4$, concentrated and purified by flash chromatography on silica gel using a gradient of 0-30% of EtOAc in hexanes as the solvent to furnish 11.2 g of compound 2. $^1$H NMR (CDCl$_3$, ppm): δ 7.87 (d, J=8.6 Hz, 2H), 7.54 (d, J=8.6 Hz, 2H), 7.00 (m, 1H), 6.47 (m, 1H), 5.56 (m, 1H), 5.21 (s, 1H), 5.18 (d, J=9.7 Hz, 1H), 4.89 (s, 1H), 4.79 (dd, J=4.0, 12.9 Hz, 1H), 4.69 (dm, J=12.9 Hz, 1H), 3.60 (s, 3H), 3.56 (m, 1H), 3.21 (s, 3H), 2.93 (dd, J=8.0, 15.2 Hz, 1H), 2.79 (dd, J=6.5, 15.2, 1H).

Method B

To a solution of 1.67 g (3.24 mmol) of compound 2 in THF (80 mL) at 0° C. was added 370 mg (9.75 mmol) of LiAlH$_4$ in portions, and the reaction mixture was stirred for 20 minutes. After the aqueous quench and extractive workup, the product was purified by flash chromatography on silica gel using a gradient of 0-30% of EtOAc in hexanes as the solvent to furnish 895 mg of diol 3. $^1$H NMR (CDCl$_3$, ppm): δ 7.62 (d, J=8.4 Hz, 2H), 7.47 (d, J=8.4 Hz, 2H), 7.02 (m, 1H), 6.48 (m, 1H), 5.65 (m, 1H), 5.03 (d, J=10.0 Hz, 1H), 4.96 (d, J=16 Hz, 1H), 4.87 (s, 1H), 4.75 (dd, J=5.6, 12.1 Hz, 1H), 4.34 (dd, J=5.0, 12.1 Hz, 1H), 3.76-3.65 (ser m, 3H), 3.57 (m, 1H), 3.39 (m, 1H), 2.63 (m, 2H), 2.02 (dd, J=7.6, 14.2 Hz, 1H), 1.89 (dd, J=7.6, 14.2 Hz, 1H), 1.64 (s, 1H).

Method C

To a solution of 217 mg (0.47 mmol) of diol 3 in DCM (10 mL) was added 148 mg (1.42 mmol) of 2,2-dimethoxypropane followed by 3.6 mg (0.01 mmol) of PPTS. The reaction mixture was stirred overnight, concentrated, and the crude product was purified by flash chromatography on silica gel using a gradient of 0-30% of EtOAc in hexanes as the solvent to furnish 185 mg of acetal 4. $^1$H NMR (CDCl$_3$, ppm): δ 7.77 (d, J=8.4 Hz, 2H), 7.52 (d, J=8.4 Hz, 2H), 7.02 (m, 1H), 6.48 (m, 1H), 5.63 (m, 1H), 5.15 (m, 2H), 5.06 (d, J=16.8 Hz, 1H), 4.81 (dd, J=4.3, 12.8 Hz, 1H), 4.57 (d, J=12.6 Hz, 1H), 3.67 (d, J=12.5 Hz, 1H), 3.58 (d, J=11.7 Hz, 1H), 3.52 (d, J=12.5 Hz, 1H), 3.46 (d, J=13.7 Hz, 1H), 2.98 (m, 1H), 2.16 (dd, J=8.0, 14.4 Hz, 1H), 1.98 (dd, J=6.7, 14.4 Hz, 1H), 1.31 (s, 3H), 1.20 (s, 3H).

Method D (a) To a solution of 1.75 g (3.51 mmol) of acetal 4 in THF (35 mL) at 0° C. was added 42.2 mL (21.1 mmol) of 0.5 M solution of 9-BBN in THF. The reaction mixture was stirred at RT overnight, chilled to 0° C., and treated with 3.0 M NaOH (30 mL) and $H_2O_2$ (30 mL). The mixture was stirred for 7 hours, diluted with equal volume of water, and extracted with EtOAc (3 times). The organic phase was washed with water and brine, dried over $Na_2SO_4$ and concentrated. The crude product was passed through a plug of silica gel using a gradient of 0-5% of MeOH in DCM as the solvent.

(b) To a solution of 2.0 g (3.88 mmol) of the above product in DCM (60 mL) at 0° C. was added 1.36 mL (9.68 mmol) of Et$_3$N, followed by 0.39 mL (5.04 mmol) of MsCl. The reaction was stirred at 0° C. for 1 hour, diluted with equal volume of water, and extracted with DCM (3 times). The organic phase was washed with water and brine, dried over Na$_2$SO$_4$ and concentrated. The resulting compound 5 (2.36 g) was used without further purification. LCMS (MH$^+$)=595.3; retention time=4.63 min.

Method E

To a solution of 120 mg (0.20 mmol) of compound 5 in THF (2.0 mL) at −30° C. was added 0.242 mL (0.242 mmol) of 1M potassium tert-butoxide in THF. The reaction was stirred at −30° C. for 20 min, diluted with equal volume of water, and extracted with EtOAc (2 times). The organic phase was washed with water and brine, dried over Na$_2$SO$_4$ and concentrated. The crude product was purified by PTLC using 2% MeOH in DCM as the solvent to furnish 70 mg of compound 6. $^1$H NMR (CDCl$_3$, ppm): δ 7.52-7.44 (ser m, 4H), 7.08 (m, 1H), 6.38 (m, 1H), 5.20 (d, J=4.9, 12.6 Hz, 1H), 4.91 (d, J=12.6 Hz, 1H), 4.03 (d, J=11.5 Hz, 1H), 3.94 (dd, J=1.6, 11.8 Hz, 1H), 3.37 (dd, J=1.4, 11.5 Hz, 1H), 2.97 (dd, J=1.4, 11.8 Hz, 1H), 2.56 (m, 1H), 2.48 (d, J=4.6 Hz, 1H), 2.44 (m, 1H), 1.92 (m, 1H), 1.68 (m, 1H), 1.42 (s, 3H), 1.31 (s, 3H), 1.23 (m, 1H), 1.11 (m, 1H). LCMS (MH$^+$)=499.3; retention time=5.03 min.

Method F

Compound 6 (344 mg, 0.691 mmol) was dissolved in 60% aqueous acetic acid (15 mL) with 2.0 mL of DCM added to increase solubility. The reaction mixture was stirred overnight, diluted with 10 volumes of water, and then extracted with DCM (2 times). The organic phase was washed with water and brine, dried over Na$_2$SO$_4$ and concentrated. The product was purified by PTLC using 1:1 mixture of EtOAc and hexanes as the solvent to furnish 280 mg of diol A. $^1$H NMR (CDCl$_3$, ppm): δ 7.55-7.41 (m, 4H), 7.08 (m, 1H), 6.41 (m, 1H), 5.17 (dd, J=4.7, 12.6 Hz, 1H), 4.91 (d, J=12.6 Hz, 1H), 3.84 (d, J=11 Hz, 1H), 3.77 (d, J=11.3 Hz, 1H), 3.71 (d, J=11 Hz, 1H), 3.49 (s, 1H), 3.20 (d, J=11.3 Hz, 1H), 2.83 (d, J=4.6 Hz, 1H), 2.62 (d, J=13.3 Hz, 1H), 1.98-1.89 (m, 3H), 1.66 (m, 1H), 1.25 (m, 2H).

SCHEME 2

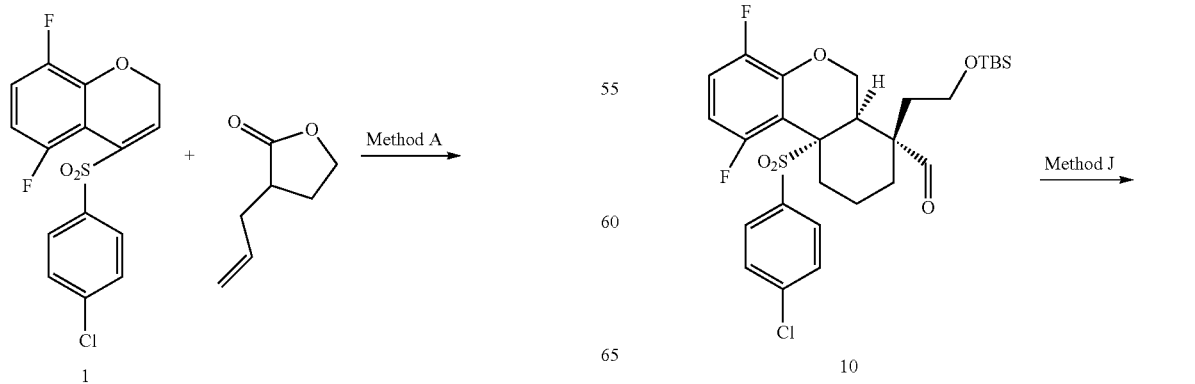

-continued

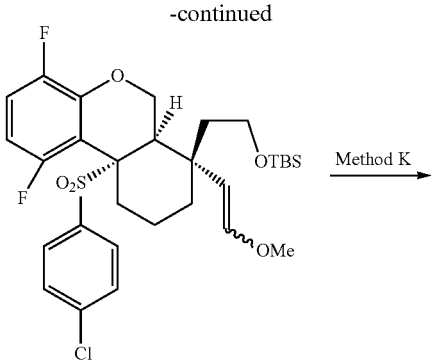

11

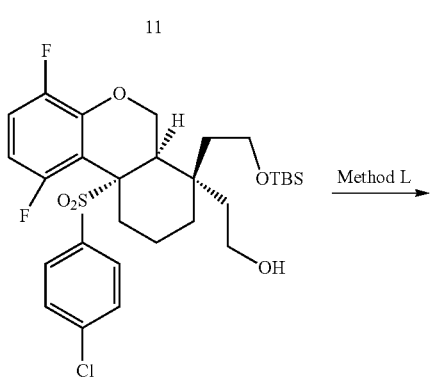

12

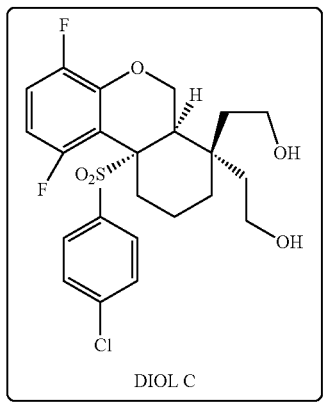

DIOL C

Scheme 2

Method G

To 2.6 mL of 1 M borane-THF complex in THF was added 503 mg (6.13 mmol) of cyclohexene at 0° C. The resulting mixture was stirred for 1 hour at 0° C. and as white precipitate was observed, additional 1.0 mL of THF was added. Compound 7, prepared according to Method A, was added in 4.0 mL of THF dropwise. The reaction was allowed to warm up to RT and stirred for 3 hours. The reaction mixture was cooled to 0° C. and treated with a mixture of 503 mg (6.1 mmol) of sodium acetate in 5.0 mL of MeOH, followed by a mixture of 416 mg of ICl in 3.0 mL of MeOH. The resultant reaction mixture was stirred for 30 minutes, quenched with NaHSO₃ (600 mg dissolved in 3.0 mL water), followed by 10 mL of saturated aqueous solution of NH₄Cl. Reaction mixture was extracted with EtOAc (3×30 mL). Combined organic phase was washed with brine, dried over MgSO₄ and concentrated. The residue was purified by flash chromatography on silica gel using a gradient of 0-30% of EtOAc in hexanes as the solvent to furnish 1.05 g of iodide 8. $^1$H NMR (CDCl₃, ppm): δ 7.75 (d, J=8.7 Hz, 2H), 7.53 (d, J=8.7 Hz, 2H), 7.07 (s, 1H), 6.45 (s, 1H), 5.01 (dd, J=5.13, 13.2 Hz, 1H), 4.73 (s, 1H), 4.36 (dm, J=13 Hz, 1H), 4.27 (m, 1H), 4.14 (m, 2H), 3.29 (d, J=4.9 Hz, 1H), 3.24 (m, 1H), 4.30 (m, 1H), 3.02 (m, 1H), 2.26 (m, 1H), 1.93-1.75 (m, 1H), 1.66-1.58 (m, 2H).

Method H

To a solution of 480 mg (1.03 mmol) of compound 9, prepared according to method E from iodide 8, in THF (18 mL) at 0° C. was added 2.05 mL (2.5 mmol) of 1M solution of LiAlH₄ in THF. The reaction was stirred at 0° C. for 1 hour. After the aqueous quench and extraction with EtOAc, the organic phase was washed with water and brine, dried over MgSO₄ and concentrated. The residue was purified by flash chromatography on silica gel using a gradient of 0-60% of EtOAc in hexanes as the solvent to furnish 433 mg of diol B. $^1$H NMR (CDCl₃, ppm): δ 7.54-7.41 (m, 4H), 7.06 (m, 1H), 6.36 (m, 1H), 5.28 (d, J=12.5 Hz, 1H), 5.14 (dd, J=5.1, 12.5 Hz, 1H), 3.66-150 (ser m, 4H), 2.74 (d, J=4.9 Hz, 1H), 2.62 (d, J=12.9 Hz, 1H), 2.04-1.88 (m, 3H), 1.70-1.59 (m, 3H), 1.29-1.09 (m, 3H).

Method I (a) To a solution of 5.15 g (11.0 mmol) of compound 9 in DCM (100 mL) at −78° C. was added 15.4 mL of 1M solution of DIBAL-H in toluene. The reaction was stirred at −78° C. for 1 hour, quenched by the addition of EtOAc and warmed to RT. Saturated aqueous solution of sodium potassium tartrate was added and the mixture was stirred for 2 hours prior to the extraction with DCM (2 times). The organic phase was washed with water and brine, dried and concentrated to furnish 5.2 g of intermediate lactol.

(b) The above material was dissolved in DCM (150 mL) and 2,6-lutidine (3.79 g, 35 mmol), and TBDMSOTf (5.08 mL, 22.1 mmol) was added at 0° C. The reaction was stirred at 0° C. for 1 hour, washed with saturated aqueous solution of NaHCO₃, dried over Na₂SO₄, and concentrated. Aldehyde 10 (3.0 g) was isolated by flash chromatography on silica gel using 20% of EtOAc in hexanes as the solvent. $^1$H NMR (CDCl₃, ppm): δ 9.62 (s, 1H), 7.54-7.43 (m, 4H), 7.08 (m, 1H), 6.39 (m, 1H), 5.12 (dd, J=5.1, 12.8 Hz, 1H), 4.52 (d, J=12.8 Hz, 1H), 3.53 (dd, J=4.8, 6.9 Hz, 1H), 3.00 (d, J=4.9 Hz, 1H), 2.68 (d, J=13.4 Hz, 1H), 2.18 (m, 1H), 1.95 (m, 1H), 1.86 (m, 1H), 1.74 (m, 1H), 1.58 (m, 2H), 1.37 (m, 1H), 1.28 (m, 1H), 0.80 (s, 9H), −0.05 (s, 3H), −0.06 (s, 3H).

Method J

Methoxymethyltriphenylphosphonium chloride (5.17 g, 15.1 mmol) was slurried in 65 mL of THF and cooled to −70° C. 15.1 mL (15.1 mmol) of 1M solution of t-BuOK in THF was added slowly such that the internal temperature did not exceed −40° C. A solution of 2.94 g (5.034 mmol) of aldehyde 10 in 25 mL of THF was added slowly maintaining the internal temperature below −40° C. Further THF (5 mL) was used to rinse the equipment. The mixture was stirred overnight over which period it was allowed to warm up to RT. After the quench with water and extraction with EtOAc, the organic phase was washed with water and brine, dried over Na₂SO₄ and concentrated. The crude product was purified by flash chromatography on silica gel using a gradient of 0-20% of EtOAc in hexanes as the solvent to furnish 2.03 g of enol ether 11 as a mixture of isomers. $^1$H NMR (CDCl$_3$, ppm): δ 7.52 (d, J=8.7 Hz, 2H), 7.45 (d, J=8.7 Hz, 2H), 7.04 (m, 1H), 6.36 (m, 1H), 5.84 (d, J=7.1 Hz, 0.5H), 5.06 (dd, J=5.5, 12.5 Hz, 1H), 4.74 (d, J=17.2 Hz, 0.5H), 4.71 (d, J=17.2 Hz, 0.5H), 4.16 (d, J=7.4 Hz, 0.5H), 3.6 (s, 2H), 3.55 (s, 1H), 3.48 (m, 2H), 2.95 (d, J=5.5 Hz, 0.4H), 2.69 (d, J=12.8 Hz, 0.6H), 2.02 (m, 0.5H), 1.89-1.74 (ser m, 2H), 0.75 (s, 6H), 0.74 (s, 3H), −0.13 (s, 2H), −0.14 (s, 2H), −0.15 (s, 1H), −0.16 (s, 1H).

Method K

To a solution of 1.81 g (2.97 mmol) of compound 11 in THF (10 mL) was slowly added at 0° C. a solution of 1.13 g (3.55 mmol) of mercury (II) acetate in 10 mL of water. The mixture was stirred overnight at ambient temperature. The reaction mixture was cooled down to 0° C. and treated with a mixture of 469 mg (12.4 mmol) of NaBH$_4$ and 10 mL of saturated aqueous solution of K$_2$CO$_3$. The mixture was stirred for 10 minutes at 0° C., extracted with EtOAc (2 times), washed with water and brine. The organic phase was dried over Na$_2$SO$_4$ and concentrated. The product was purified by flash chromatography on silica gel using a gradient of 0-35% of EtOAc in hexanes as the solvent to furnish 1.57 g of compound 12. $^1$H NMR (CDCl$_3$, ppm): δ 7.52-7.41 (m, 4H), 7.05 (m, 1H), 6.35 (m, 1H), 5.10 (dd, J=5.6, 13.0 Hz, 1H), 4.72 (d, J=12.6 Hz, 1H), 3.81 (t, J=7.1 Hz, 2H), 3.51 (m, 2H), 2.74 (d, J=5 Hz, 1H), 2.65 (d, J=13 Hz, 1H), 1.99-1.86 (m, 2H), 1.78-1.66 (m, 2H), 1.52-1.29 (m, 4H), 1.64-1.58 (m, 2H), 0.77 (s, 9H), −0.10 (s, 3H), −0.11 (s, 3H).

Method L

To a solution of 785 mg (1.31 mmol) of compound 12 in THF (12 mL) was slowly added 2.62 mL of 1M solution of TBAF in THF. The mixture was stirred for 2 hours, quenched with water and extracted with EtOAc (2 times). The organic phase was washed with water and brine, dried over Na$_2$SO$_4$ and concentrated. The crude product was recrystalized from DCM to furnish 585 mg of diol C. $^1$H NMR (CDCl$_3$, ppm): δ 7.53-7.41 (m, 4H), 7.06 (m, 1H), 6.36 (m, 1H), 5.11 (dd, J=5.1, 12.5 Hz, 1H), 4.73 (d, J=12.5 Hz, 1H), 3.83 (t, J=6.6 Hz, 1H), 3.64-3.48 (m, 2H), 2.76 (d, J=5.1 Hz, 1H), 2.67 (d, J=12.5 Hz, 1H), 2.01-1.88 (m, 2H), 1.78-1.31 (ser m, 6H).

SCHEME 3

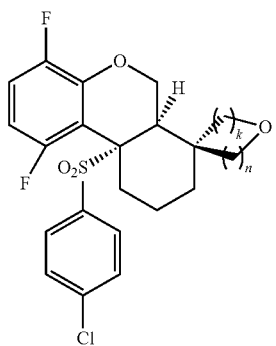

13

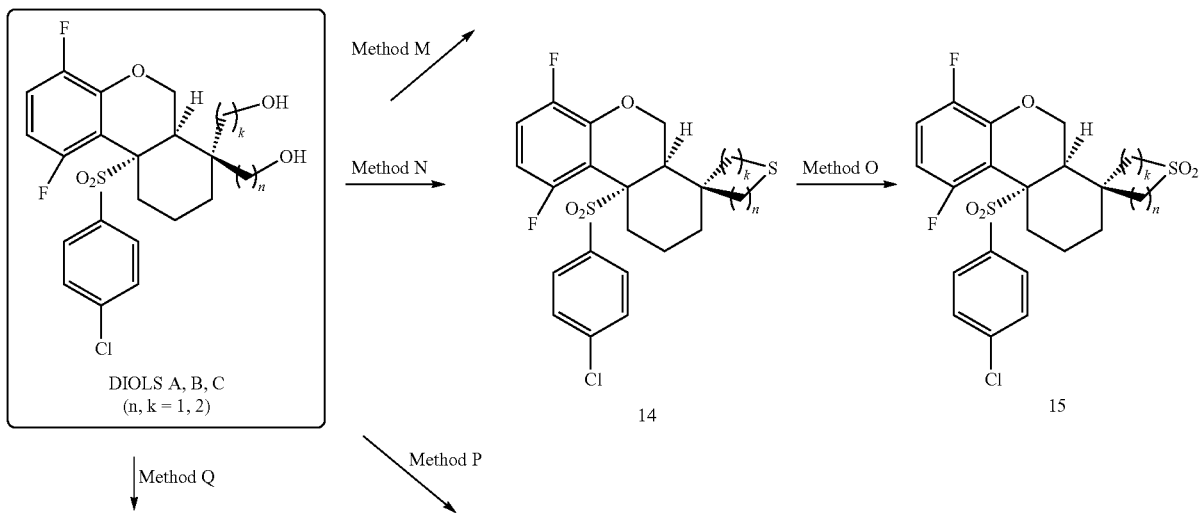

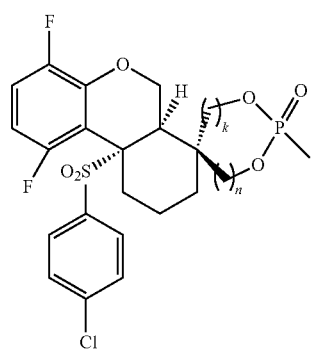

17

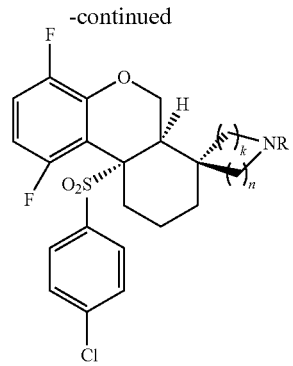

16

Scheme 3

Method M

To a solution of 216 mg (0.419 mmol) of diol A in DCM (15.0 mL) at 0° C. was added 106 mg (1.05 mmol) of Et$_3$N, followed by 58 mg (0.50 mmol) of MSCl. The reaction was stirred at 0° C. for 1 hour, diluted with water, extracted with DCM (3 times). The organic phase was washed with water and brine, dried over Na$_2$SO$_4$ and concentrated.

The crude product was dissolved in 20 mL of DMF and treated at 0° C. with 50.2 mg (1.26 mmol) of a suspension of NaH in mineral oil. After stirring for 2 hours, the reaction mixture was diluted with water and extracted with DCM. The organic phase was washed with water and brine, dried over Na$_2$SO$_4$ and concentrated. The product was isolated from the reaction mixture by flash chromatography on silica gel using a gradient 0-60% of EtOAc in hexanes as the solvent, and further chromatographed on Chiralpak™ AD column using IPA as the solvent, to furnish in the order of elution, 12 mg of (−)-enantiomer and 14 mg of (+)-enantiomer of compound 13 (k=n=1). $^1$H NMR (CDCl$_3$, ppm): δ 7.53-7.44 (m, 4H), 7.09 (m, 1H), 6.33 (m, 1H), 5.31 (dd, J=5.1, 12.5 Hz, 1H), 5.19 (d, J=12.5 Hz, 1H), 4.77 (d, J=6.5 Hz, 1H), 4.58 (d, J=5.8 Hz, 1H), 4.22 (d, J=6.5 Hz, 1H), 3.81 (d, J=6.5 Hz, 1H), 2.58 (m, 1H), 2.55 (d, J=4.3 Hz, 1H), 2.39 (d, J=13.1 Hz, 1H), 1.93 (m, 1H), 1.76-1.60 (m, 2H), 1.2-1.07 (m, 1H).

Method N (a) To a solution of 110 mg (0.233 mmol) of diol C in DCM (5 mL) at 0° C. was added 80.1 mg (0.699 mmol) of MsCl followed by 70.7 mg (0.699 mmol) Et$_3$N. The reaction was stirred at 0° C. for 0.5 hour and quenched by the addition of water. The reaction mixture was extracted with DCM (2 times), organic phase was washed with water, 1M HCl, and brine, dried over Na$_2$SO$_4$ and concentrated.

(b) The product from the previous step (150 mg) was dissolved in 4.0 mL of dry EtOH, and treated with 36 mg (1.467 mmol) of Na$_2$S and 0.5 mL of pyridine. The reaction mixture was refluxed for 3 hours, cooled, quenched by addition of water, and extracted with DCM. The organic phase was washed with water and brine, dried over Na$_2$SO$_4$ and concentrated. The product was purified by flash chromatography on silica gel using a gradient of 0-50% of EtOAc in hexanes as the solvent to furnish 88 mg of compound 14 (k=n=2). $^1$H NMR (CDCl$_3$, ppm): δ 7.53-7.41 (m, 4H), 7.06 (m, 1H), 6.34 (m, 1H), 5.16 (dd, J=5.3, 12.8 Hz, 1H), 4.87 (d, J=12.8 Hz, 1H), 2.95 (td, J=2.5, 13.4 Hz, 1H), 2.71-2.58 (ser m, 2H), 2.36 (d, J=13.7 Hz, 1H), 2.31 (d, J=5.1 Hz, 1H), 2.27-2.17 (m, 2H), 2.09 (d, J=13.9 Hz, 1H), 1.94 (m, 1H), 1.82 (m, 1H), 1.64 (m, 1H), 1.47 (d, J=13.2 Hz, 1H), 1.35 (d, J=13.7 Hz, 1H), 1.20 (q, J=13.5 Hz, 1H), 1.01 (t, J=13.4 Hz, 1H). LCMS (MH$^+$)=485.3; retention time=5.27 min.

Method O

To a mixture of 83 mg (0.171 mmol) of compound 14 (k=n=2) in 2.0 mL of acetone and 0.5 mL of water was added 211 mg (0.343 mmol) of Oxone™. The reaction was stirred over 2 days and extracted with DCM (2 times). The organic phase was washed with water and brine, dried over Na$_2$SO$_4$ and concentrated. The product was purified by flash chromatography on silica gel using a gradient of 0-70% of EtOAc in hexanes as the solvent to furnish 77 mg of compound 15 (k=n=2). $^1$H NMR (CDCl$_3$, ppm): δ7.51-7.44 (m, 4H), 7.08 (m, 1H), 6.38 (m, 1H), 5.19 (dd, J=5.3, 13.1 Hz, 1H), 4.79 (d, J=13 Hz, 1H), 3.15 (td, J=14.1, 3.5 Hz, 1H), 2.97 (m, 2H), 2.85 (td, J=14.4, 3.5 Hz, 1H), 2.76-2.64 (m, 4H), 2.52 (d, J=5.1 Hz, 1H), 2.30 (m, 1H), 2.19 (m, 1H), 1.98 (m, 1H), 1.75 (m, 1H), 1.46 (m, 1H), 1.22 (m, 1H). LCMS (MH$^+$)=517.3; retention time=4.32 min.

Method P (a) To a solution of 73 mg (0.155 mmol) of diol B in a mixture of DCM 2.5 mL and pyridine (1.0 mL) at 0° C. was added DMAP, then TsCl. The reaction was stirred at 0° C. for 1 hour, quenched by the addition of water, extracted with DCM (2 times), washed with water and brine. The organic phase was dried over Na$_2$SO$_4$ and concentrated, and bis-tosylate of diol B was purified by flash chromatography on silica gel using 60% of EtOAc in hexanes as the solvent to furnish 12 mg of bis-tosylate of diol B.

(b) 12 mg (0.015 mmol) of bis-tosylate of diol B was dissolved in 1.0 mL of DMF and treated with 11.5 mg (0.077 mmol) of trifluoromethanesulfonamide and 10.6 mg (0.077 mmol) of K$_2$CO$_3$. The reaction mixture was stirred at 70° C. overnight, cooled, quenched by the addition of water, extracted with DCM (2 times). The organic phase was washed with water and brine, dried over Na$_2$SO$_4$ and concentrated. The product was purified by PTLC using 60% of EtOAc in hexanes as the solvent to furnish 5.0 mg of triflamide 16 (k=1, n=2). $^1$H NMR (CDCl$_3$, ppm): δ 7.54-7.46 (m, 4H), 7.10 (m, 1H), 6.43 (m, 1H), 5.24 (dd, J=4.9, 13.0 Hz, 1H), 4.62 (d, J=13 Hz, 1H), 3.67 (d, J=10.1 Hz, 1H), 3.60 (t, J=9.3 Hz, 1H), 3.43-3.33 (m, 2H), 2.75 (d, J=4.7 Hz, 1H), 2.63 (d, J=12.9 Hz, 1H), 2.10-1.93 (ser m, 2H), 1.86 (d, J=14.6 Hz, 1H), 1.75 (m, 1H), 1.42 (m, 1H), 1.33-1.18 (ser m, 2H). LCMS (MH$^+$)=586.3; retention time=5.24 min.

Method Q

To a mixture of 50 mg (0.11 mmol) of diol A in THF (1.5 mL) at −78° C. was added 19 mg (0.24 mmol) of pyridine, followed by 19 mg (1.12 mmol) of methylphosphonic dichloride. The reaction mixture was stirred for 2 hours over which period of time it was allowed to warm up to RT. Water was added and the reaction mixture was extracted with DCM. The organic phase was washed with water and brine, dried over $Na_2SO_4$ and concentrated. The product was purified by PTLC using EtOAc as the solvent to afford separated diastereomers of phosphonate 17 (k=1, n=1). Diastereomer 1, 25 mg. $^1$H NMR (CDCl$_3$, ppm): δ 7.53-7.44 (m, 4H), 7.10 (m, 1H), 6.43 (m, 1H), 5.19 (dd, J=4.6, 13.2 Hz, 1H), 4.82 (dd, J=4.2, 11.2 Hz, 1H), 4.73 (m, 1H), 4.68 (d, J=13 Hz, 1H), 3.7 (ddd, J=2.7, 11.2, 19.8 Hz, 1H), 3.45 (ddd, J=2.7, 11.2, 20.5 Hz, 1H), 2.64 (d, J=13.7 Hz, 1H), 2.54 (d, J=4.6 Hz, 1H), 2.42 (d, J=11 Hz, 1H), 1.97 (m, 1H), 1.77 (m, 1H), 1.53 (d, J=17.9 Hz, 3H), 1.29 (m, 2H). Diastereomer 2, 18 mg. $^1$H NMR (CDCl$_3$, ppm): δ 7.56-7.43 (m, 4H), 7.12 (m, 1H), 6.45 (m, 1H), 5.27 (dd, J=4.6, 13.0 Hz, 1H), 4.73 (d, J=13 Hz, 1H), 4.31 (t, J=11.5 Hz, 1H), 4.17 (dd, J=6.0, 12.8 Hz, 1H), 4.09 (m, J=4.09 Hz, 1H), 3.67 (ddd, J=1.6, 11.8, 19.8 Hz, 1H), 2.67 (d, J=4.4 Hz, 1H), 2.60 (m, 1H), 2.37 (m, 1H), 1.97 (m, 1H), 1.80-1.71 (m, 1H), 1.57 (d, J=9.7 Hz, 3H), 1.27 (m, 2H).

Assay

The pharmacological properties of the compounds of this invention may be evaluated by a number of pharmacological assays. The exemplified pharmacological assays, which are described later, have been carried out with the compounds according to the present invention.

Gamma-secretase activity was determined as described by Zhang et al. (Biochemistry, 40 (16), 5049-5055, 2001), which is herein incorporated by reference. Activity is expressed either as a percent inhibition or as the concentration of compound producing 50% inhibition of enzyme activity.

Reagents

Antibodies W02, G2-10, and G2-11 were obtained from Dr. Konrad Beyreuther (University of Heidelberg, Heidelberg, Germany). W02 recognizes residues 5-8 of Aβ peptide, while G2-10 and G2-11 recognize the specific C-terminal structure of Aβ 40 and Aβ 42, respectively. Biotin-4G8 was purchased from Senetec (St. Louis, Mo.). All tissue culture reagents used in this work were from Life Technologies, Inc., unless otherwise specified. Pepstatin A was purchased from Roche Molecular Biochemicals; DFK167 was from Enzyme Systems Products (Livermore, Calif.).

cDNA Constructs, Tissue Culture, and Cell Line Construction

The construct SPC99-Ion, which contains the first 18 residues and the C-terminal 99 amino acids of APP carrying the London mutation, has been described (Zhang, L., Song, L., and Parker, E. (1999) J. Biol. Chem. 274, 8966-8972). Upon insertion into the membrane, the 17 amino acid signal peptide is processed, leaving an additional leucine at the N-terminus of Aβ. SPC99-lon was cloned into the pcDNA4/TO vector (Invitrogen) and transfected into 293 cells stably transfected with pcDNA6/TR, which is provided in the T-REx system (Invitrogen). The transfected cells were selected in Dulbecco's modified Eagle's media (DMEM) supplemented with 10% fetal bovine serum, 100 units/mL penicillin, 100 g/mL streptomycin, 250 g/mL zeocin, and 5 g/mL blasticidin (Invitrogen). Colonies were screened for Aβ production by inducing C99 expression with 0.1 g/mL tetracycline for 16-20 h and analyzing conditioned media with a sandwich immunoassay (see below). One of the clones, designated as pTRE.15, was used in these studies.

Membrane Preparation

C99 expression in cells was induced with 0.1 g/mL tetracycline for 20 h. The cells were pretreated with 1 M phorbol 12-myristate 13-acetate (PMA) and 1 M brefeldin A (BFA) for 5-6 h at 37° C. before harvesting. The cells were washed 3 times with cold phosphate-buffered saline (PBS) and harvested in buffer A containing 20 mM Hepes (pH 7.5), 250 mM sucrose, 50 mM KCl, 2 mM EDTA, 2 mM EGTA, and Complete protease inhibitor tablets (Roche Molecular Biochemicals). The cell pellets were flash-frozen in liquid nitrogen and stored at −70° C. before use.

To make membranes, the cells were resuspended in buffer A and lysed in a nitrogen bomb at 600 psi. The cell lysate was centrifuged at 1500 g for 10 min to remove nuclei and large cell debris. The supernatant was centrifuged at 100000 g for 1 h. The membrane pellet was resuspended in buffer A plus 0.5 M NaCl, and the membranes were collected by centrifugation at 200000 g for 1 h. The salt-washed membrane pellet was washed again in buffer A and centrifuged at 100000 g for 1 h. The final membrane pellet was resuspended in a small volume of buffer A using a Teflon-glass homogenizer. The protein concentration was determined, and membrane aliquots were flash-frozen in liquid nitrogen and stored at −70° C.

γ-Secretase Reaction and Aβ Analysis

To measure γ-secretase activity, membranes were incubated at 37° C. for 1 h in 50 μL of buffer containing 20 mM Hepes (pH 7.0) and 2 mM EDTA. At the end of the incubation, Aβ 40 and Aβ 42 were measured using an electrochemiluminescence (ECL)-based immunoassay. Aβ 40 was identified with antibody pairs TAG-G2-10 and biotin-W02, while Aβ 42 was identified with TAG-G2-11 and biotin-4G8. The ECL signal was measured using an ECL-M8 instrument (IGEN International, Inc.) according to the manufacturer's instructions. The data presented were the means of the duplicate or triplicate measurements in each experiment. The characteristics of γ-secretase activity described were confirmed using more than five independent membrane preparations.

As shown below in the Table, the compounds of the invention had a membrane IC$_{50}$ in the range of 5 nM to 421 nM.

| Structure | Aβ₄₀, IC₅₀, nM | Method for synthesis | Analytical Characterization |
|---|---|---|---|
| (structure) | 66.6 | E | Compound 6 in text |
| (structure) | 10.1 | M | Compound 13 in text |
| (structure) | 13.9 | M | $^1$H NMR (CDCl$_3$, ppm): δ 7.55-7.40 (m, 4 H), 7.09 (m, 1 H), 6.38 (m, 1 H), 5.17 (dd, J = 5.3, 12.5 Hz, 1 H), 4.72 (d, J = 12.5 Hz, 1 H), 3.92 (td, J = 2.9, 8.4 Hz, 1 H), 3.88 (d, J = 8.9 Hz, 1 H), 3.65 (q, J = 8.8 Hz, 1 H), 3.50 (d, J = 9.1 Hz, 1 H), 2.72 (d, J = 5.2 Hz, 1 H), 2.61 (d, J = 11.5 Hz, 1 H), 1.96 (m, 1 H), 1.83 (m, 1 H), 1.72 (m, 2 H), 1.39 (t, J = 12.5 Hz, 1 H), 1.30-1.12 (ser m, 2 H) |
| (structure) | 228.0 | E | LCMS (MH$^+$) = 469.3; retention time = 4.61 min. |

TABLE-continued

| Structure | Aβ₄₀, IC₅₀, nM | Method for synthesis | Analytical Characterization |
|---|---|---|---|
| 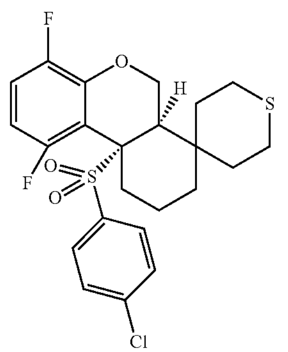 [SMILES: O=S(=O)(c1ccc(Cl)cc1)[C@@]12CCCC3(CCSCC3)[C@@H]1COc1c(F)ccc(F)c12] | 26.4 | N | Compound 14 in text |
| 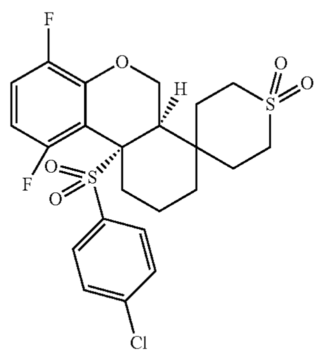 [SMILES: O=S1(=O)CCC2(CCC[C@@]3(S(=O)(=O)c4ccc(Cl)cc4)c4c(F)ccc(F)c4OC[C@@H]23)CC1] | 57.7 | O | Compound 15 in text |
| 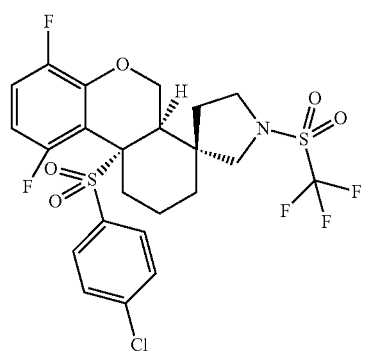 [SMILES: O=S(=O)(N1CC[C@]2(CCC[C@@]3(S(=O)(=O)c4ccc(Cl)cc4)c4c(F)ccc(F)c4OC[C@@H]23)C1)C(F)(F)F] | 23.3 | P | Compound 16 in text |
| 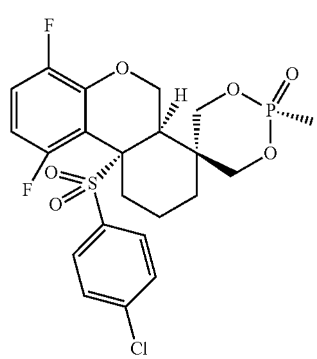 [SMILES: C[P@]1(=O)OC[C@]2(CCC[C@@]3(S(=O)(=O)c4ccc(Cl)cc4)c4c(F)ccc(F)c4OC[C@@H]23)CO1] | 9.5 | Q | Compound 17 diastereomer 1 in text |

TABLE-continued

| Structure | Aβ₄₀, IC₅₀, nM | Method for synthesis | Analytical Characterization |
|---|---|---|---|
| (structure) | 421.0 | Q | Compound 17 diastereomer 2 in text |
| (structure) | 397.0 | Q | LCMS (MH⁺) = 553.3; retention time = 4.19 min. |
| (structure) | 79.0 | Q | LCMS (MH⁺) = 553.3; retention time = 4.12 min. |
| (structure) | 5.4 | Q | LCMS (MH⁺) = 533.3; retention time = 4.00 min. |

While the present invention has been described in conjunction with the specific embodiments set forth above, many alternatives, modification and variations thereof will be apparent to those of ordinary skill in the art. All such alternatives, modifications and variations are intended to fall within the spirit and scope of the present invention.

What is claimed:

1. A compound of the Formula (I):

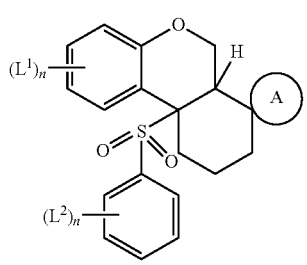

(I)

wherein:

A is a 4 to 7 membered spirocyclic ring comprising at least one heteroatom selected from the group consisting of N, O, S, S(O)$_2$, P(O)R$^1$, and N—S(O)$_2$—R$^1$, wherein the spirocyclic ring is optionally substituted with 1 to 3 substituents selected from the group consisting of C1-3alkyl and =O, with the proviso that A is not 1,3-dioxolane;

R$^1$ is C1-6alkyl optionally substituted with halo;

Each L$^1$ is independently selected from the group consisting of 1) C1-3alkyl optionally substituted with halo, and 2) halo;

Each L$^2$ is independently selected from the group consisting of 1) C1-3alkyl optionally substituted with halo, and 2) halo; and n is selected from 0 to 3 at each occurrence of n.

2. The compound according to claim 1, wherein L$^1$ and L$^2$ are halo.

3. The compound according to claim 1, wherein L$^1$ is fluoro and L$^2$ is chloro.

4. The compound according to claim 1, wherein the compound is of Formula (Ia)

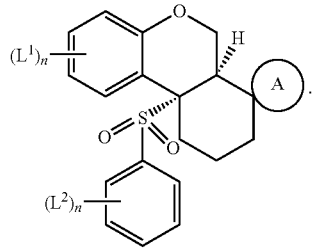

(Ia)

5. The compound according to claim 1, wherein the compound is of Formula (II)

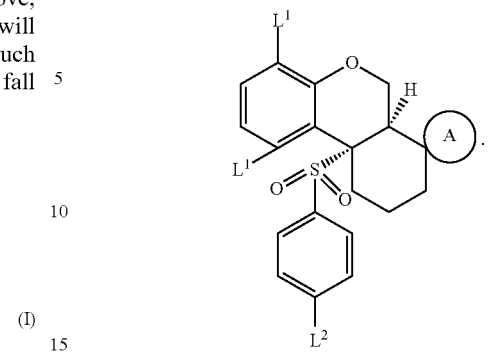

(II)

6. The compound according to claim 5, wherein A is a 4 to 7 membered spirocyclic ring comprising at least one O heteroatom.

7. The compound according to claim 5, wherein A is a 4 to 7 membered spirocyclic ring comprising one N heteroatom.

8. The compound according to claim 5, wherein A is a 4-7 membered spirocyclic ring comprising one S heteroatom.

9. The compound according to claim 5, wherein A is a 4-7 membered spirocyclic ring comprising one S(O)$_2$ heteroatom.

10. The compound according to claim 5, wherein A is a 6-7 membered spirocyclic ring comprising two O heteroatoms and the heteroatom P(O)R$^1$.

11. The compound according to claim 10, wherein R$^1$ is methyl.

12. The compound according to claim 5, wherein L$^1$ and L$^2$ are halo.

13. The compound according to claim 12, wherein L$^1$ is fluoro and L$^2$ is chloro.

14. A compound which is selected from the group consisting of:

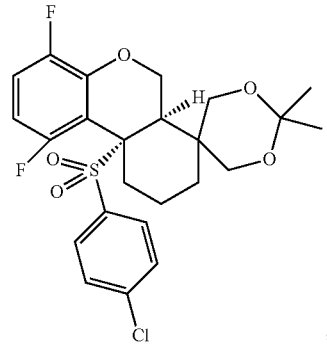

33
-continued
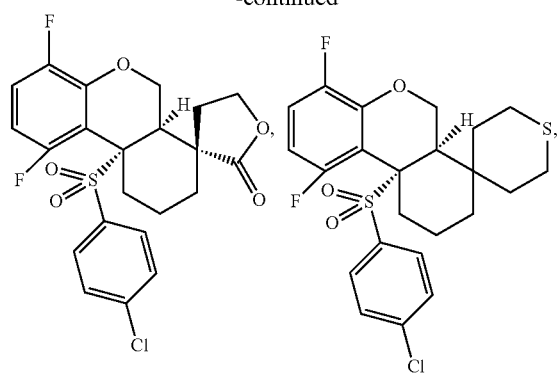
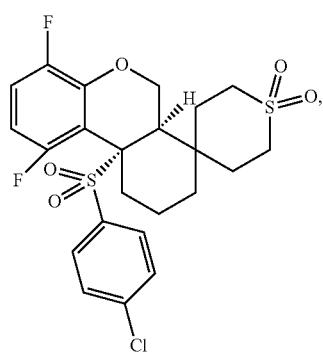
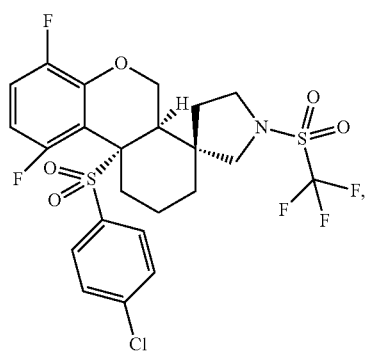
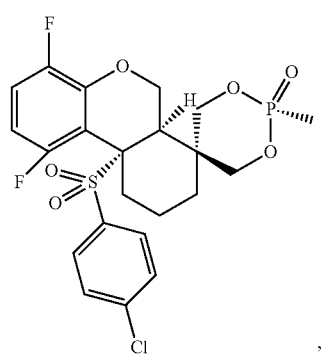
34
-continued
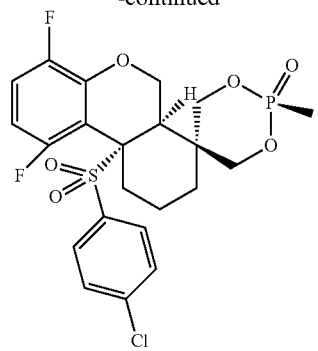
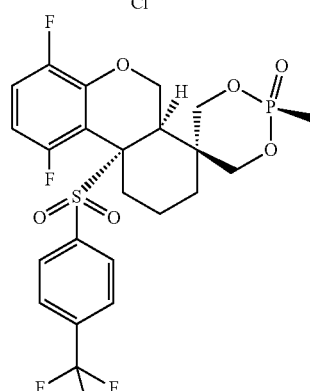
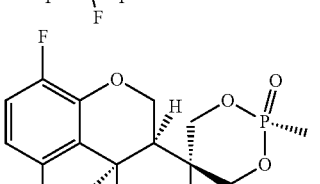
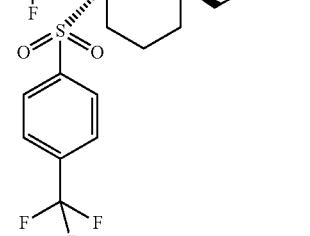
and
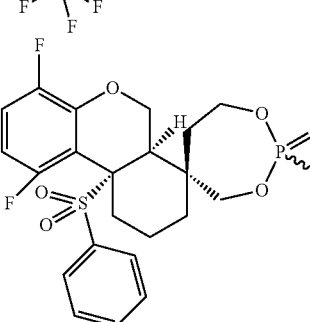
15. A pharmaceutical composition comprising a compound according to claim 1 and a pharmaceutically acceptable carrier.
16. A pharmaceutical composition comprising the compound according to claim 14 and a pharmaceutically acceptable carrier.
* * * * *